United States Patent [19]
Hilton

[11] Patent Number: 5,206,220
[45] Date of Patent: Apr. 27, 1993

[54] SOLUBLE AND STABLE SOURCES OF TYROSINE, CYSTEINE AND GLUTAMINE FOR TOTAL PARENTERAL NUTRITION

[75] Inventor: Mary A. Hilton, Louisville, Ky.

[73] Assignee: Research Corporation Technologies, Inc., Tucson, Ariz.

[21] Appl. No.: 742,782

[22] Filed: Aug. 8, 1991

Related U.S. Application Data

[63] Continuation-in-part of Ser. No. 512,698, Apr. 23, 1990, abandoned.

[51] Int. Cl.$^5$ ............................................. A61K 37/02
[52] U.S. Cl. .................................................. 514/19
[58] Field of Search ........................................ 514/19

[56] References Cited

U.S. PATENT DOCUMENTS 4,491,589  1/1985  Dell et al. ............................ 514/400
4,927,808  5/1990  Kitahara et al. ..................... 514/19

FOREIGN PATENT DOCUMENTS 0416108  3/1991  European Pat. Off. .

OTHER PUBLICATIONS

Furukawa et al., (1990), *Amino Acids, Chemistry, Biology and Medicine*, (Lubec et al.) pp. 1114–1118.
Adibi (1987) *Metabolism* 36: 1001–1011.
Anderson et al. (1983) *Proc. Natl. Acad. Sci.* 80: 707–711.
Chessex et al. (1985) *J. Pediatr.* 106: 111–117.
Dahlstrom et al. (1988) *J. Pediatr. Gastroenterol Nutr.* 7: 748–754.
Helms et al. (1987) *J. Pediatr.* 110: 466–470.
Magnusson et al. (1989) *Metabolism* 38: 957–961.
Stegink (1977) *Clinical Nutrition Update: Amino Acids*, (Greene et al., eds.) pp. 192–198.
Stegink (1986) *Energy and Protein Needs during Infancy* (Fomon et al., eds.( Academic Press, Inc., NY, 183–206.
Stehle et al. (1985) *Nutr. Spec. Supp.* 4: 116–123.
Stehle et al. (1988) *J. Nutrition* 118: 1470–1474.

*Primary Examiner*—Michael G. Wityshyn
*Assistant Examiner*—Choon P. Koh
*Attorney, Agent, or Firm*—Scully, Scott, Murphy & Presser

[57] ABSTRACT

The present invention provides soluble and/or stable sources of tyrosine, cysteine and glutamine for use in total parenteral nutrition (TPN), as well as a gradual release source of glutamic acid. In particular, these sources are gamma-glutamyltyrosine (γ-GluTyr) gamma-glutamylcysteine derivatives (γ-GluCys) and gamma-glutamylglutamine (γ-GluGln). This invention provides TPN formulations, and methods of formulating and using such solutions containing γ-GluTyr, γ-GluCys and/or γ-GluGln to provide adequate nutritional levels of tyrosine, cysteine or glutamine during TPN.

42 Claims, No Drawings

SOLUBLE AND STABLE SOURCES OF TYROSINE, CYSTEINE AND GLUTAMINE FOR TOTAL PARENTERAL NUTRITION

CROSS REFERENCE TO RELATED APPLICATION

This application is a continuation-in-part of U.S. patent application Ser. No. 512,698 filed Apr. 23, 1990, now abandoned.

FIELD OF THE INVENTION

The present invention provides soluble and/or stable sources of tyrosine, cysteine and glutamine for use in total parental nutrition (TPN) as well as a sustained-release source of glutamic acid. In particular, these sources are gamma-L-glutamyl-L-tyrosine (γ-GluTyr) gamma-L-glutamyl-L-cysteine (γ-GluCys) gamma-L-glutamyl-L-glutamine (γ-GluGln) and their derivatives, water soluble peptides that, after parenteral administration, are hydrolysed by tissue enzymes to release free tyrosine and glutamic acid, free cysteine and glutamic acid, or free glutamine and glutamic acid, respectively. These peptides are formulated into amino acid solutions for administration in TPN, to produce normal plasma levels of tyrosine, cysteine, glutamine and glutamic acid in humans and animals. This invention provides TPN formulations, and methods of formulating and using TPN solutions containing γ-GluTyr, γ-GluCys, γ-GluGln either singly or in combination.

BACKGROUND OF THE INVENTION

Total parenteral nutrition (TPN) is designed to meet the nutritional requirements for humans and animals unable to obtain proper enteral nutrition orally or via the gastrointestinal tract. TPN solutions must provide all nutrients including carbohydrates, amino acids (as a substitute for protein), lipids, vitamins, and other essential compounds such as electrolytes and trace elements. The optimal desirable composition for TPN solutions is well known yet cannot always be achieved for each component because of intrinsic limitations imposed by the physiochemical properties of that component. Such limitations include poor solubility and instability during storage. In the case of TPN amino acid solutions, the optimal composition is one that produces a normal pattern of plasma amino acids (i.e., a normal plasma aminogram). The plasma amino acid levels are determined by the balance between the rate of administration of each amino acid and its rate of utilization. For example, a normal plasma aminogram corresponds to one produced after digestion of dietary protein and hepatic release of amino acids or one produced in normal breast-fed infants. Examples of normal plasma amino acid patterns in normal breast-fed infants is described by Wu, P. Y. K. (1986) *J. Pediatr.* 109: 347-349, and in adults is described by Perry, R. T. et al. (1969) *Clin. Chim. Acta* 25: 53-58.

However, because of the limited solubility of tyrosine and cyst(e)ine as well as the instability of cysteine asparagine and glutamine, solutions using free amino acids cannot be produced containing adequate, let alone optimal, amounts of these amino acids, as deduced from current knowledge of amino acid metabolism. Moreover, high levels of glutamate may lead to excitotoxicity, [Barinaga, M. (1990) *Science* 247: 20-22].

The relative insolubility of tyrosine in aqueous solutions at physiological pH has long presented problems in formulating TPN amino acid solutions. The ability to provide optimal tyrosine levels in TPN solutions is important in normalizing plasma levels of this amino acid. In infants, especially low-birth weight and premature infants, the metabolic pathway for conversion of phenylalanine, an essential amino acid, to tyrosine is not developed sufficiently to allow adequate conversion. Good tyrosine nutrition in early development may be crucial since it is a precursor of several hormones and neurotransmitters. Since the enzyme system which converts phenylalanine to tyrosine is primarily a liver enzyme, there may be particular disease conditions in adults, children and animals, especially liver diseases, in which the formation of tyrosine is impaired. Thus, the need for a TPN solution that achieves optimal (or adequate) plasma levels of tyrosine is highly desirable.

Typical amino acid solutions for TPN in pediatric patients contain tyrosine at about 44 mg/dl (e.g., Aminosyn-PF 10%, Abbott Laboratories), about the maximum amount soluble at the pH required for parenteral administration and an amount inadequate to attain normal plasma levels of tyrosine in patients, especially infants receiving TPN. Numerous alternatives have long been sought to increase tyrosine solubility or to provide other sources of tyrosine but none has satisfactorily solved the problem. The prior art teaches several soluble alternatives for tyrosine which can be formulated into TPN solutions, including use of high levels of phenylalanine, use of N-acetyl-L-tyrosine (NAcTyr), L-glycyl-L-tyrosine (GlyTyr), L-alanyl-L-tyrosine (AlaTyr) or general dipeptides containing tyrosine where the two amino acids have a normal peptide linkage joining the α-carboxyl group of the first residue and the α-amino group of the second residue and have the general formula X-Tyr or Tyr-Y wherein X is alanine, arginine, histidine, lysine, serine, glycine or glutamate and Y is arginine, histidine, glycine or glutamate. Of these dipeptides, all exhibit better aqueous solubility than tyrosine, and all suffer from instability in aqueous solution due to a tendency to form cyclic diketopiperazines. Of the known tyrosine-containing dipeptides, only AlaTyr was investigated for utility in TPN [Stegink, L. D. (1986) in *Energy and Proteins Needs during Infancy*, (S. J. Fomon and W. C. Heird, Eds.) Academic Press, Inc., NY, p183-206].

Formation of diketopiperazines may be a concern as illustrated in the case of aspartame, an unstable methyl ester of a dipeptide of aspartic acid and phenylalanine which limits the shelf-life of soft drinks in which it is used as a sweetener, because of loss of sweetness with formation of a diketopiperazine. While not a concern in foods ingested orally, data establishing the safety of diketopiperazines administered intravenously, as in TPN into very small infants, is unavailable.

Aminosyn-PF 10% contains high levels of phenylalanine based on the assumption that phenylalanine can serve as a precursor for tyrosine. While this may be a fair assumption for some adults, newborn infants appear unable to convert significant amount of phenylalanine into tyrosine. For example, breast-fed infants have a plasma ratio of phenylalanine to tyrosine (Phe/Tyr) of about 0.6, low birthweight infants fed pooled human milk have a ratio of about 0.7–0.8, and infants fed solely by TPN, using amino acid mixtures like Aminosyn-PF 10% or other compositions presently available, have plasma Phe/Tyr ratios that are abnormally high, ranging from about 2.2-3.7. Since phenylalanine and tyrosine compete for transport from the blood into tissues, including the brain, these high levels of phenylalanine relative to tyrosine only exacerbate the deficit in tissue tyrosine. This can clearly compromise the growth and development of the infant.

Moreover, there are also disease conditions in adults and children, such as those involving impairment of liver function, where metabolic conversion of phenylalanine to tyrosine may be disturbed. Such patients would benefit from improved TPN solutions supplying adequate amounts of tyrosine. Hence, replacement of tyrosine by phenylalanine may be counterproductive as a method to increase plasma tyrosine levels.

Another source of tyrosine examined because of its increased aqueous solubility, and which avoids the problem of diketopiperazine formation, is NAcTyr. The use of NAcTyr in TPN for pre-term neonates has been reported (Helms, R. A. et al. (1987) *J. Pediatr.* 110: 466–470). A study of NAcTyr utilization in TPN by Magnusson, I. et al. (1989) *Metabolism* 38: 957–961, showed that in adults the plasma levels of tyrosine four hours after administration of 5 g tyrosine in a 10 mg/ml solution were nearly the same as the basal tyrosine levels (63 vs. 51 $\mu$mol/l, respectively). However, while the NAcTyr levels increased dramatically in the same time frame (from 9 to 256 $\mu$mol/l), 56% of the administered NAcTyr was excreted in the urine within 4 h. In another study by Stegink, supra, rats infused with NAcTyr at a rate of 0.5 mmol/kg/day or 2 mmol/kg/day showed that after 24 h of TPN, the plasma tyrosine levels were unchanged at the low infusion rate and merely increased two-fold at the higher rate. Although the studies using NAcTyr in rats indicate some utilization of the tyrosine, there appears to be a species difference between the rat and the human, since humans cannot release tyrosine efficiently from NAcTyr. Thus, despite its increased solubility, NAcTyr is not satisfactory to replace or supplement tyrosine in TPN solutions. NAcTyr suffers the further disadvantage of not being a normal product of human metabolism, and therefore the safety of its long term use, especially in high risk infants, is a concern.

AlaTyr has also been investigated as an alternative source of tyrosine in amino acid solutions for TPN (Stegink, supra). Like NAcTyr, AlaTyr is sufficiently soluble under aqueous, physiological conditions to deliver potentially adequate nutritional levels of free tyrosine. However, administration of AlaTyr to rats at a rate of 0.5 mmol/kg/day or 2 mmol/kg/day indicated that after 24 h of administration, the plasma tyrosine levels were unchanged at the lower rate and merely increased two-fold at the higher rate. Renal excretion of AlaTyr also occurred but at a slightly lower rate than NAcTyr loss. AlaTyr as well as the soluble dipeptides discussed above suffer a major disadvantage in that they are unstable in aqueous solution, especially upon the prolonged storage periods to which TPN amino acid solutions are often subjected. This instability appears to be caused by diketopiperazine formation (Stegink, supra). Hence, $\alpha$-carboxyl-linked peptides cannot be added to TPN amino acid solutions subjected to long storage periods and are, thus, best added just prior to administration of the TPN solution, a practice that leaves room for error and contamination.

In a survey of di- and tri-peptides for TPN, a large number of glycyl-Z dipeptides were examined for utility in TPN [Adibi, S. (1987) *Metabolism* 36:1001–1011], where Z was one of the 20 common amino acids. In particular, upon administration of AlaTyr or GlyTyr in rats at a rate of 0.5 mmol/kg, plasma tyrosine levels did not increase as rapidly for GlyTyr as for AlaTyr. In both cases, the levels reached the same value at longer times. As mentioned above, the GlyTyr dipeptide also suffers the disadvantage of being unstable during storage in aqueous solution.

Accordingly, the present invention provides a soluble source of tyrosine which does not exhibit the disadvantages of the compounds known in the prior art for TPN. The subject tyrosine source, $\gamma$-GluTyr, readily supplies adequate and optimal amounts of tyrosine to the patient, is stable upon prolonged storage periods in aqueous solutions used for TPN since it does not contain an $\alpha$-carboxyl linkage, and is a naturally occurring dipeptide, being generated during the $\gamma$-glutamyl cycle as described by Meister (1973) *Science* 180 33–39. $\gamma$-GluTyr is readily metabolized to release free tyrosine at least in part via degradation by $\alpha$-glutamyl transpeptidase. Since $\gamma$-GluTyr is a normal product of metabolism, it provides a safe source of tyrosine in vivo, with little potential for producing toxicity in high-risk infants and other patients, including humans and animals.

Like tyrosine, cysteine has been difficult to supply in adequate amounts via TPN. When supplied as cysteine in an aqueous solution at neutral pH in the presence of oxygen, cysteine is spontaneously converted to cystine with release of hydrogen peroxide as shown below:

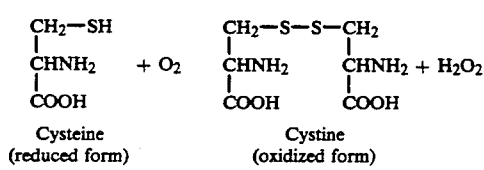

The designation cyst(e)ine refers either to the oxidized or reduced form of cysteine. Cystine is quite insoluble in water (1 mg/dl) especially at the neutral pH required for TPN. Thus, despite the solubility of cysteine, its conversion to cystine coupled with the insolubility of cystine, makes it difficult to supply adequate cysteine by TPN.

Although cyst(e)ine is not considered a dietary "essential" amino acid for children or adults, it may be essential for neonates. This amino acid is formed via a metabolic pathway called "trans-sulfuration." In this process the "essential" amino acid, methionine, donates its sulfur atom to serine, forming cysteine. The metabolic pathway to cysteine, which involves five different enzyme-catalyzed reactions, is shown below in abbreviated form:

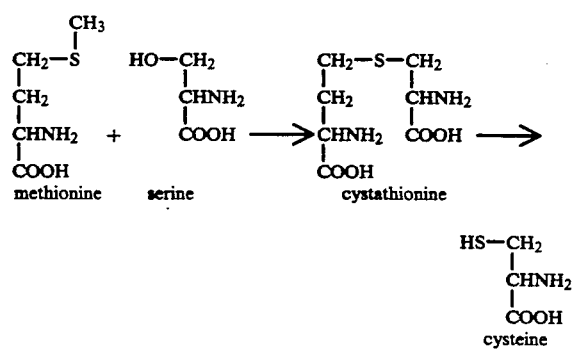

Cystathionase, the enzyme which catalyzes the final step in the biosynthesis of cysteine, is primarily a liver enzyme and is fully operative only after birth. Thus, the neonate, and particularly the pre-term neonate, cannot meet the need for cysteine via the normal biosynthetic route. The intermediate cystathionine accumulates and is excreted in the urine, thus causing cysteine to become a nutritionally "essential" amino acid for these infants.

Cysteine has a number of important intracellular functions in addition to its role in protein synthesis: (a) Cysteine is required for the conversion of the vitamin, pantothenic acid, to coenzyme A, its metabolically active form. (b) Cysteine is a metabolic precursor of the amino sulfonic acid, taurine. Taurine is currently included in TPN solutions, reducing some of the dietary need for cysteine. (c) Cysteine is limiting for the biosynthesis of the tripeptide, glutathione (gamma-glutamyl-cysteinylglycine), which plays a major role in protecting tissues against oxidative damage. Glutathione (GSH) is also important in the detoxification of xenobiotics and in the maintenance of functional thiol groups in proteins. [Meister, A. et al. (1983) Ann. Rev. Biochem. 52: 711-760].

Water-soluble GSH, and fat-soluble vitamin E, are important antioxidants and may be of special significance in protecting infants exposed to hyperbaric oxygen. A cysteine deficiency can lead to export of GSH from the liver to replenish plasma cyst(e)ine through degradation of plasma GSH [Meister, A. (1988) J. Biol. Chem. 263: 17205-17208]. Depletion of liver GSH below a critical level may lead to numerous matabolic aberrations.

One major concern in the delivery of cyst(e)ine via TPN is that this amino acid has been shown to be lethal when fed to weanling rats at a level of 15.7 g N/kg basal diet, and neurotoxic when administered in a single subcutaneous dose (1.2 mg/kg body weight) to 4-day-old rats, and in a single intraperitoneal dose (10 mmol/kg body weight) to mice [Anderson, M. E. et al. (1987) Methods Enzymol. 143: 313-325]. The reasons for this toxicity are not clear, but it appears to be associated with extracellular cyst(e)ine. Thus, a means of delivering cyst(e)ine intracellularly is desired.

Several methods have been used or suggested in the prior art for provision of adequate cysteine during TPN. However, these methods suffer many disadvantages which can be overcome by providing γ-GluCys for use in TPN solutions.

Cysteine-hydrochloride (cysteine-HCl) has been administered as a separate solution, not combined in the mixture of the other amino acids used in TPN. This soluble form of cysteine is stable at low pH. The amount of HCl which high-risk infants can tolerate is limited and this, in turn, limits the amount of cysteine-HCl which may be used in TPN. Cysteine-HCl in TPN has been implicated in the production of acidosis in some treated low-birth-weight infants [Heird, W. C. (1988) Pediatr. 81: 41-50].

Another source of cysteine examined for use in TPN has been N-acetylcysteine (NAcCys). However, like NAcTyr, NAcCys was not found to be a satisfactory replacement source for cysteine (Magnussen et al.). In particular, the plasma levels of cysteine four hours after administration of 5 g cysteine in a 200 mg/ml solution decreased relative to the basal cysteine level (134 vs 207 μmol/l). However, while the NAcCys levels increased dramatically in the same time frame (from 2 to 488 μmol/l), 11% of the administered NAcCys was excreted in the urine within 4 h. Stegink et al. also reported large urinary losses of N,N'-bis-acetylcystine when administered for TPN and concluded that this compound was not a suitable alternative source for cysteine in TPN.

Further to the Adibi et al. study of di- and tri-peptides in TPN as described above, no dipeptides containing cysteine having utility in TPN were disclosed.

GSH has also been used as a source of cysteine during long-term TPN in the growing rat [Neuhauser-Berthold, M. et al. (1988) Metabolism 37: 796-801]. There have been no reports of GSH stability upon prolonged storage under TPN storage conditions. Further, GSH does not appear to be transported into cells whereas γ-GluCys derivatives are transported (as γ-L-glutamyl-L-cystine, i.e., γ-Glu(Cys)$_2$; or N,N'-bis-(γ-L-glutamyl)cysteine, i.e. (γ-GluCys)$_2$) [Anderson, M. E. et al. (1983) Proc. Natl. Acad. Sci. USA 80: 707-711. Thus γ-GluCys and its derivatives may provide a more efficient means to increase the GSH content in tissues as well as to provide a stable source of cysteine.

A further concern in current TPN formulations is the inclusion of high levels of methionine in these solutions, with the misguided view that large supplements of methionine will substitute for the inadequate cysteine levels in TPN solutions. High intake of methionine is associated with hepatotoxicity [Benevenga, N.J. (1974) J. Agric. Food Chem. 22: 2-9]. In view of this, there is a alarming discrepancy between reported plasma ratios of cysteine to methionine (Cys/Met) of 10/1 in breast-fed infants [Gaull, G. E. et al. (1977) J. Pediatr. 90: 348-355] and of 0.6 in infants on TPN supplemented with L-cysteine-HCL [Zlotkin, S. H. et al. (1981) Am. J. Clin. Nutr. 34: 914-923]. The use of γ-GluCys and derivatives in TPN solutions make it possible to increase the cysteine supply in a non-toxic form, and to reduce the amount of methionine needed in these solutions to achieve more normal Cys/Met ratios.

Accordingly, the present invention provides a soluble source of cysteine which does not exhibit the disadvantages of the compounds known in the prior art for TPN. The subject cysteine source, γ-GlyCys and derivatives described below, readily supplies adequate and optimal amounts of cysteine to the patient, is stable upon prolonged storage periods in aqueous solutions used for TPN since it lacks an α-carboxyl linkage. Moreover, like γ-GluTyr, γ-GluCys is a naturally occurring dipeptide, which can be generated by the tissue enzymes, γ-glutamyl transpeptidease or by γ-glutamylcysteine synthetase. As a normal product of metabolism, γ-GluCys provides a safe source of vivo, with little potential for producing toxicity in high risk infants and other patients, including humans and animals.

Glutamine is yet another amino acid which has been difficult to supply in adequate amounts via TPN. Although glutamine is present in plasma at the highest concentration of any amino acid, glutamine is not included in TPN because of its instability in aqueous solutions. In particular, glutamine breaks down in aqueous solution to form pyroglutamic acid with a release of toxic ammonia according to the reaction below:

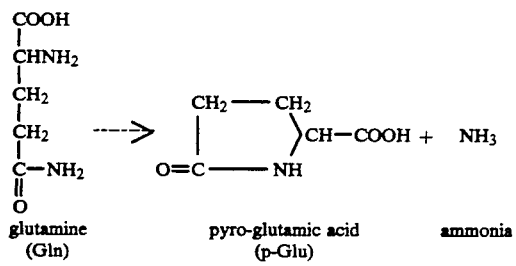

glutamine (Gln) → pyro-glutamic acid (p-Glu) + ammonia

Hence, TPN solutions containing glutamine which are stored even for short lengths of time can accumulate toxic ammonia. While a fresh glutamine solution can be added to the TPN solution, this greatly increases the risk of contamination and error in formulation. Thus, TPN solutions in present use do not contain glutamine.

Because glutamine cannot be included in mixtures of amino acids for TPN, high levels of glutamate are substituted on the assumption that in vivo conversion of glutamate to glutamine occurs. However as discussed below high levels of glutamate are neurotoxic and should be avoided. The normal plasma ratio of glutamine (Gln) to glutamate (Glu), based on mean values is about 27:1 (Perry et al. (1969) *Clin. Chim. Acta* 25:53–58), whereas in infants maintained for one week on TPN, the Gln:Glu ratio is reduced to 1.1:1 (Aminosyn PF) and 0.7:1 (Neopham) (Coran et al. (1989) *J. Pediatr. Enter. Nutr.* 11:368–377). This reduction appears to be due to both a decrease in plasma glutamine and an increase in plasma glutamate.

The markedly reduced ratio of plasma Gln:Glu does not provide sufficient glutamine for proper nutrition of the gut. Lack of glutamine appears to be a factor in gut pathology associated with the difficulty many infants experience in adapting to oral feeding after prolonged TPN. In fact, studies in rats showed that TPN lacking glutamine lead to decreased villus height in the intestine, whereas inclusion of glutamine in TPN preserved the normal architecture of gut villi (*Surg. Form.* 37:56–58 (1986)). In these studies freshly prepared glutamine was added to the TPN mixture.

One method used in the prior art to supply glutamine has been via the dipeptides glycylglutamine (GlyGln) and alanylglutamine (AlaGln) (Adibi, supra). Like other dipeptides these compounds are also unstable during prolonged storage in aqueous solution due to the tendency to form cyclic diketopiperazines.

Accordingly, the present invention provides a stable source of glutamine which does not exhibit the disadvantages of the compounds known in the prior art for TPN. The subject glutamine source, γ-GluGln, readily supplies adequate and optimal amounts of glutamine to the patient, is stable upon prolonged storage periods in aqueous solutions used for TPN since it does not contain an α-carboxyl linkage, and is a naturally occurring dipeptide, being generated during the γ-glutamyl cycle as described by Meister, supra. γ-GluGln is readily metabolized to release free glutamine, at least in part via degradation by γ-glutamyl transpeptidase. Since γ-GluGln is a normal product of metabolism, it provides a safe source of glutamine in vivo, with little potential for producing toxicity in high-risk infants and other patients, including humans and animals.

Another important advantage in the use of γ-GluTyr γ-GluCys and γ-GluGln in TPN is that upon hydrolysis in vivo, glutamic acid is gradually released. This allows reduction of the rather large amount of free glutamic acid normally present in TPN solutions (for example there is 820 mg/dL in Aminosyn-PF 10%). Thus, glutamic acid can be reduced proportionately by the amount administered as γ-GluTyr, γ-GluCys or γ-GluGln. Reduction of free glutamic acid in TPN is important in light of the concern about the excitotoxicity and neurotoxicity of free glutamic acid especially as related to the use of monosodium glutamate (MSG) as a food additive. The safe use of glutamic acid, which has been called an "excitotoxin," should be considered in determining the amounts of glutamic acid administered by TPN to infants, who may be more susceptible than adults to nerve damage by glutamate (Barinaga supra). Thus, in addition to the benefits relative to stability and solubility of tyrosine, cysteine and glutamine, the present invention provides a means to reduce free glutamic acid in TPN solutions while still providing adequate nutritional levels of glutamic acid.

SUMMARY OF THE INVENTION

The present invention provides an improved method for obtaining normal plasma levels of free tyrosine in a patient during total parenteral nutrition (TPN) by administering to that patient γ-glutamyltyrosine (γ-GluTyr) in a TPN solution in an amount effective to obtain adequate or optimal plasma levels of free tyrosine in the treated patient. Preferably γ-GluTyr is γ-L-glutamyl-L-tyrosine. Specifically the patient may be a human or an animal. For humans, this method of obtaining tyrosine is especially useful in low birth weight infants with an immature metabolic system and in any age patient with a disease condition that prevents adequate biosynthesis of tyrosine, e.g., by interfering with the normal conversion of phenylalanine to tyrosine.

The present invention further provides an improved method for obtaining normal plasma levels of cysteine in a patient during TPN by administering γ-glutamylcysteine (γ-GlyCys), or certain derivatives thereof, in a TPN solution in an amount effective to obtain adequate or optimal plasma levels of cysteine in the treated patient. Preferably γ-GluCys is provided as γ-L-glutamyl-L-cystine or N,N′-bis-(γ-L-glutamyl)-L-cysteine. Specifically the patient can be a human or an animal.

Still another aspect of the invention provides an improved method for obtaining normal plasma levels of glutamine in a patient during TPN by administering γ-glutamylglutamine (γ-GluGln) in a TPN solution in an amount effective to obtain adequate or optimal plasma levels of glutamine in the treated patient. Preferably, γ-GluGln is γ-L-glutamyl-L-glutamine. Moreover, the level of γ-GluGln can be provided at a level to obtain normal plasma Gln:Glu ratios. Specifically, the patient can be a human or an animal.

Moreover, a method for obtaining optimal nutrition via TPN solutions is provided which embodies all or part of the aspects of the invention as summarized above, i.e., administration of γ-GluTyr, γ-GluCys, γ-GluGln, or any combination of these three compounds can be provided simultaneously in the same TPN solution.

Another aspect of this invention provides TPN solutions, including amino acid solutions for use in TPN, wherein tyrosine, cysteine or glutamine is supplemented or replaced by γ-GluTyr, γ-GluCys or γ-GluGln, respectively, in an amount effective to provide normal plasma levels of tyrosine, cysteine or glutamine, respectively. TPN solutions with γ-GluTyr, γ-GluCys, γ-

GluGln or any combination of these three are also contemplated. In any of these solutions phenylalanine, methionine, and glutamic acid can be reduced by an appropriate amount.

DETAILED DESCRIPTION OF THE INVENTION

The present invention provides an improved method for obtaining normal plasma levels of tyrosine, cysteine or glutamine in a patient during total parenteral nutrition (TPN) by supplementing or replacing the tyrosine, cysteine or glutamine in a TPN solution to be administered with an amount of γ-glutamyltyrosine ( γ-GluTyr), γ-glutamylcyst(e)ine (γ-GluCys) or γ-glutamylglutamine (γ-GluGln), respectively, effective to produce adequate or optimal plasma levels of free tyrosine, cyst(e)ine or glutamine in the treated patient, i.e., a level of tyrosine, cyst(e)ine or glutamine sufficient to meet the nutritional needs of the patient. This method of TPN is provided for animals and humans, and especially to those animals or humans in a condition with a reduced ability to produce or metabolize tyrosine, cysteine, or glutamine biosynthetically. However, the present method of TPN is not limited to such individuals, since it readily provides all the amino acids necessary to sustain proper nutrition and is thus useful for any individual requiring intravenous administration of nutrients, supplementation of amino acids and other nutrients, or administration of TPN solutions and the like.

Moreover, the present method may be modified to simultaneously provide free tyrosine, free cysteine, free glutamine, or any combination of these three compounds to satisfy nutrition requirements in a patient as described above. Further, in supplementing or replacing tyrosine, cysteine and/or glutamine as provided herein, free glutamic acid in TPN solutions can be proportionally reduced. Likewise, the phenylalanine and methionine content of TPN solutions can be reduced if necessary or desirable.

As used herein "total parenteral nutrition" or "TPN" refers to a regimen of obtaining nutrition by a parenteral route when enteral (oral or gastrointestinal) nutrition is impossible or impaired. Such conditions may occur in certain disease states, in new born infants, or comatose patients. TPN is generally administered to the patient via an intravenous route, either in a central or peripheral vein. Any other known route of administering TPN is also contemplated by this invention, e.g., intraperitoneal. TPN solutions are usually administered continuously by intravenous infusion. The dosage of nutrients administered during TPN is determined by the total body weight and status of the patient. The dosage is then typically expressed as the dosage of nutrients/kg body weight/24 h period. One skilled in the art can readily determine the proper dosage and rate of administration to achieve the desired nutritional state. The optimal mixture of amino acids is one which will produce a normal pattern of amino acids in the plasma.

The nutritive requirements for TPN are well known, TPN solutions having first been developed in the 1950s. These solutions must provide all nutrients including an energy source (e.g. carbohydrates), amino acids (as a substitute for protein), lipids, vitamins, and other essential components such as electrolytes and trace elements. In general, TPN solutions are prepared as separate groups of components, i.e., as an amino acid solution or a dextrose solution, and then mixed together before administration at a ratio to give final nutrient concentrations to meet the optimal nutritional requirements for the patient. Typically, the present practice of TPN provides a solution of amino acids which can be mixed with a solution of dextrose (i.e., carbohydrate) and other necessary supplements. While the improved method of administering TPN in the instant invention is described for TPN amino acid solutions, it should be understood that all the considerations for formulating these solutions apply equally to any TPN formulation, especially solutions or compositions including multiple groups of components, e.g. a TPN solution containing premixed carbohydrates and amino acids, a TPN solution containing premixed amino acids, electrolytes and trace elements, etc. In other words, for any type of TPN solution with any combination of nutrients, then whenever tyrosine, cysteine and/or glutamine is present or should be present (i.e., considered as necessary nutrients), the tyrosine, cysteine and/or glutamine can be supplemented, replaced or augmented by γ-GluTyr, γ-GluCys, and/or γ-GluGln respectively, in accordance with the present invention.

The preferred compositions for TPN solutions are well known and many commercial preparations are available. TPN amino acid solutions are usually provided as about 5-10% solutions of amino acids. The conventional TPN formulations can be used in the present invention by adding γ-GluTyr, γ-GluCys or γ-GluGln to these solutions. Alternatively, γ-GluTyr, γ-GluCys, γ-GluGln or any combination of these can be added during formulation of TPN solutions in accordance with this invention. The 20 common amino acids can be included in such solutions although some TPN products are limited to the essential and semi-essential amino acids as deemed appropriate for the exigency of the situation. The amino acid solutions can also include ornithine, citrulline and taurine if desired. For example, in pediatric formulations, 17 of the 20 common amino acids are generally included, with omission of cysteine, glutamine, and asparagine (because of their instability in solution) and addition of taurine. An example of a TPN amino acid solution is described in U.S. Pat. No. 4,491,589 which is incorporated herein by reference. Some commercial amino acid solutions include Aminosyn-PF 10% (Abbott Laboratories); FreAmine, FreAmine II, FreAmine III, TrophAmine (Kendall McGaw Laboratories, Inc.); Travasol 8.5%, Travasol 10% blend B, Travamine (Travenol Laboratories); Vamin 7% (Pharmacia Canada, Inc.); NeoAminosol, Cutter amino acid solution as well as casein and fibrin hydrolysates. Veterinarian compositions for TPN which contain γ-GluTyr, γ-GluCys or γ-GluGln in accordance with the present invention are also contemplated.

As used herein, "γ-glutamyltyrosine" or "γ-GluTyr" refers to a dipeptide formed by covalent bonding of the γ-carboxyl group of glutamic acid with the α-amino group of tyrosine. While it is metabolically preferable that the L forms of these amino acids be used, the invention is not so limited if the need arises, i.e., one or the other amino acids could be in the D form. Thus, the preferred species of γ-GluTyr is γ-L-glutamyl-L-tyrosine. This dipeptide is known to occur naturally, being synthesized during the γ-glutamyl cycle (Meister supra). Importantly, there exists a metabolic pathway for degradation of this dipeptide into its substituent amino acid residues to provide for release of free tyrosine and glutamate. This degradation mechanism involves the hydrolysis of the dipeptide by the tissue enzyme γ-glutamyl-transpeptidase.

γ-GluTyr is commercially available or may be synthesized by standard peptide chemical routes. Such synthetic methods are well known in the art and include, for example, the Merrifield method of solid phase peptide synthesis.

As used herein, "γ-GluCys" or "γ-Glutamylcysteine" refers to peptides having at least one peptide unit formed by covalent bonding of the γ-carboxyl group of glutamic acid with the α-amino group of cysteine. Given the propensity of cysteine to oxidize, the γ-GluCys is stably and preferably provided as γ-glutamylcystine, i.e., γ-Glu(Cys)$_2$, or N,N'-bis(γ-glutamyl)cystine, i.e., γ-GluCys)$_2$. While it is also preferable that the L forms of these amino acids be used, the invention is not so limited if the need arises, i.e., at least one of the amino acids may be in the D form. Nevertheless, at least one of the amino acids in these peptides is in the L form.

Thus, the preferred peptide species of γ-GluCys provided by this invention are γ-L-glutamyl-L-cysteine and N,N'-bis(γ-L-glutamyl)-L-cystine]. Both peptides are already oxidized (in the disulfide form) and thus will not oxidize further to produce $H_2O_2$ in solution or in vivo. Both peptides are freely soluble in water due to the presence of the polar glutamyl group(s). Moreover, these peptides are also stable in aqueous solution since they lack the α-carboxyl peptide linkage associated with diketopiperazine formation.

γ-GluCys and the herein defined derivatives may be synthesized by standard peptide chemical routes. Such synthetic methods are well known in the art and include, for example, the Merrifield method of solid phase peptide synthesis. Moreover, as necessary, the synthesized peptides are reduced to form the oxidized (disulfide bridged) compounds.

As used herein, "γ-glutamylglutamine" or "γ-GluGln" refers to a dipeptide formed by covalent bonding of the γ-carboxyl group of glutamic acid with the α-amino group of glutamine. While it is metabolically preferable that the L forms of these amino acids be used, the invention is not so limited if the need arises, i.e., one or the other amino acids could be in the D form. Thus, the preferred species of γ-GluGln is γ-L-glutamyl-L-glutamine. This dipeptide is known to occur naturally, being synthesized during the γ-glutamyl cycle (Meister supra). Importantly, there exists a metabolic pathway for degradation of this dipeptide into its substituent amino acid residues to provide for release of free glutamine and glutamate. This degradation mechanism involves the hydrolysis of the dipeptide by the tissue enzyme γ-glutamyl-tarnspeptidase.

γ-GluGln is commercially available or may be synthesized by standard peptide chemical routes. Such synthetic methods are well known in the art and include, for example, the Merrifield method of solid phase peptide synthesis.

Accordingly, the present invention provides a method of normalizing plasma levels of free tyrosine during TPN which comprises administering a TPN solution containing γ-GluTyr to a patient undergoing TPN treatment, wherein the free tyrosine of the TPN solution has been supplemented or replaced by γ-GluTyr at a level sufficient to satisfy the nutritional requirements of the patient. Concomitantly, a reduction in the phenylalanine and glutamic acid content of the TPN solution is possible. The patient can be a human or an animal, and is generally in a condition in which enteral feeding is ineffective to obtain proper nutrition. To prepare a TPN solution containing γ-GluTyr, the free tyrosine in such a solution is supplemented or replaced by an amount of γ-GluTyr effective to provide a sufficient nutritional level of free tyrosine, i.e., to normalize plasma tyrosine levels and plasma Phe/Tyr ratios.

In a preferred embodiment, γ-GluTyr is formulated into a TPN amino acid solution at a concentration ranging from about 150 to about 600 mg/dl, while concentrations from about 150 to 750 mg/dl are also acceptable. Any other amino acids in the solution are provided in the typical amounts for TPN solutions with the exception that the glutamic acid content may be reduced by the amount of glutamic acid calculated to be released during hydrolysis of γ-GluTyr or by any other appropriate amount compatible with maintaining an adequate, but not neurotoxic, amount of glutamic acid in the patient. Table 1 compares four formulas containing γ-GluTyr and a commercial TPN amino acid solution, showing the levels of γ-GluTyr, Tyr, Glu, Phe as well as other parameters relating to the solution. The amount of phenylalanine in TPN solutions may also be adjusted to normalize plasma Phe/Tyr ratios. Since γ-GluTyr readily dissolves in aqueous media at physiological pH, it is easily incorporated into TPN solutions without the need for special procedures. As is well known, all TPN solutions must be sterilized by a suitable method before administration.

TABLE 1

| | γ-GluTyr amounts for TPN solutions | | | | |
|---|---|---|---|---|---|
| | Formula A (mg/dL) | Formula B (mg/dL) | Formula C (mg/dL) | Formula D (mg/dL) | Aminosyn-PF 10% (mg/dL) |
| γ-GluTyr | 150 | 375 | 500 | 750 | 0 |
| Glu | 749 | 642 | 583 | 467 | 820 |
| Glu released from γ-GluTyr | 71 | 178 | 237 | 353 | |
| Total Glu | 820 | 820 | 820 | 820 | 820 |
| Tyr | 44 | 44 | 44 | 44 | 44 |
| Tyr released from γ-GluTyr | 88 | 219 | 292 | 435 | |
| Total Tyr | 132 | 263 | 336 | 479 | 44 |
| Phe equivalent of released Tyr | 80 | 200 | 266 | 319 | |
| Total Phe in solution | 347 | 215 | 215 | 215 | 427 |
| Molar Phe/Tyr ratio* | 2.88 | 0.90 | 0.70 | 0.49 | 10.79 |

*The molar ratio of the free amino acids, Phe/Tyr, in mother's milk is 0.94 [Rassin, D.K., et al., (1977) J. Pediatr 90:356-360]. This does not take into account the phenylalanine and tyrosine content of milk proteins which are digested to release amino acids in the gastrointestinal tract.

Another aspect of the present invention provides a method of normalizing plasma levels of free cyst(e)ine during TPN which comprises administering a TPN solution containing γ-GluCys to a patient undergoing TPN treatment, wherein the free cysteine of the TPN solution has been supplemented or replaced by γ-GluCys at a level sufficient to satisfy the nutritional requirements of the patient. Concomitantly, reduction in the methionine and glutamic acid content of the TPN solution is possible. The patient can be a human or an animal, and is generally in a condition in which enteral feeding is ineffective to obtain proper nutrition. To prepare a TPN solution containing γ-GluCys, the free cysteine or cystine, if present, in such a solution is supplemented or replaced by an amount of γ-GluCys effective to provide a sufficient nutritional level of free cysteine, i.e., to normalize plasma cyst(e)ine levels and plasma Cys/Met ratios.

In a preferred embodiment, γ-GluCys or the herein defined derivatives are formulated into a TPN amino acid solution at a concentration ranging from about 150 to about 600 mg/dl. Any other amino acids in the solution are provided in the typical amounts for TPN solutions with the exception that the glutamic acid content may be reduced by the amount of glutamic acid calculated to be released during hydrolysis of γ-GluCys or by any other appropriate amount compatible with maintaining an adequate, but not neurotoxic, amount of glutamic acid in the patient. Methionine levels may also be reduced, as methionine would no longer be the sole source of cysteine sulfur. Table 2 compares three formulas containing γ-GluCys$_2$ and a commercial TPN amino acid solution, showing the levels of γ-Glu(Cys)$_2$, Cys, Glu, Met as well as other parameters relating to the solution. Similar solutions can be prepared for (γ-GluCys)$_2$ or other γ-GluCys derivatives. The amount of methionine in these TPN solutions may also be adjusted. Since γ-GluCys and derivatives readily dissolve in aqueous media at physiological pH, it is easily incorporated into TPN solutions without the need for special procedures. As is well known, all TPN solutions must be sterilized by a suitable method before administration.

satisfy the nutritional requirements of the patient. Concomitantly, a reduction in the glutamic acid content of the TPN solution is possible. The patient can be a human or an animal, and is generally in a condition in which enteral feeding is ineffective to obtain proper nutrition. To prepare a TPN solution containing γ-GluGln, an effective amount of γ-GluGln is added to the TPN solution to provide a sufficient nutritional level of free glutamine, i.e., to normalize plasma glutamine levels and plasma Gln/Glu ratios. Additionally or alternatively, the amount of γ-GluGln can be adjusted to maintain normal gut physiology, or to prevent gastrointestinal distress in infants, adults or animals during a transfer from TPN to normal oral feeding.

Although free glutamine is normally omitted from TPN solutions, if present, the free glutamine can be supplemented or replaced by γ-GluGln in accordance with the present invention.

In a preferred embodiment, γ-GluGln is formulated into a TPN amino acid solution at a concentration ranging from about 150 to about 1000 mg/dl. Any other amino acids in the solution are provided in the typical amounts for TPN solutions with the exception that the glutamic acid content may be reduced by the amount of glutamic acid calculated to be released during hydrolysis of γ-GluGln or by any other appropriate amount compatible with maintaining an adequate, but not neurotoxic, amount of glutamic acid in the patient. Since γ-GluGln readily dissolves in aqueous media at physiological pH, it is easily incorporated into TPN solutions without the need for special procedures. As is well known, all TPN solutions must be sterilized by a suitable method before administration.

The present invention provides a method of simultaneously normalizing plasma levels of free tyrosine, free cysteine, free glutamine or any combination of these three compounds during TPN in accordance with the methods described above, wherein free tyrosine, free cysteine and/or free glutamine are supplemented or replaced by γ-GluTyr, γ-GluCys and/or γ-GluGln in accordance with the separate provisions of this invention

TABLE 2

| | γ-Glu(Cys)$_2$ amounts for TPN solutions | | | |
|---|---|---|---|---|
| | Formula E (mg/dL) | Formula F (mg/dL) | Formula G (mg/dL) | Aminosyn-PF 10% (mg/dL) |
| γ-Glu(Cys)$_2$ | 150 | 300 | 600 | 0 |
| Glu | 766 | 712 | 602 | 820 |
| Glu released from γ-Glu(Cys)$_2$ | 54 | 108 | 218 | — |
| Total Glu | 820 | 820 | 820 | 820 |
| Cys | | | | (67)* |
| Cys released from γ-Glu(Cys)$_2$ | 90 | 179 | 359 | |
| Met "spared" by released Cys | 111 | 220 | 442 | (82) |
| Met | 160** | 80** | 45** | 180 |
| Molar Cys/Met*** | 0.7 | 2.8 | 9.9 | 0.4 |

*Amount of cysteine-HCl suggested for use with Aminosyn-PF 10% calculated from a recommended level of 100 mg/kg/day and a total volume of TPN solution of 1.5 dL/kg/day.
**Amount of Met is arbitrary. Met should be added to maintain a positive nitrogen balance while normalizing the plasma Cys/Met ratio. Since high Met intake is associated with hepatotoxicity, it is recommended that Met be added in the minimum amount to achieve these results.
***The reported molar Cys/Met ratio in the plasma of term breast-fed infants is 10 (Gaull et al.)

Accordingly, the present invention provides a method of normalizing plasma levels of free glutamine during TPN which comprises administering a TPN solution containing γ-GluGln to a patient undergoing TPN treatment, wherein the glutamine of the TPN solution is provided by γ-GluGln at a level sufficient to tion for each of these as a single amino acid. Overall the goal is to provide optimal nutrition in the patient receiving TPN as has been herein described. Consequently, simultaneous adjustment of γ-GluTyr, γ-GluCys, γ-GluGln, phenylalanine, methionine, and glutamic acid levels, either singly or in any combination, can be effected to produce a TPN solution that satisfies the nutritional requirements of the patient.

Another embodiment of the present invention provides TPN solutions and compositions wherein tyrosine is supplemented or replaced by γ-GluTyr in an amount effective to provide a patient with a sufficient nutritional level of free tyrosine. Additionally, the amount of γ-GluTyr can provide a normal Phe/Tyr ratio, optionally by also reducing the amount of phenylalanine in the TPN solution. Further, the glutamic acid content of the TPN solutions can be reduced. In a preferred embodiment, the amount of γ-GluTyr needed for adequate nutrition is about 150 to about 600 mg/dL, while amounts of about 150 to about 750 mg/dl are also acceptable although higher levels may be required to normalize the plasma aminogram. In general tyrosine is also present, although in much lower amounts since its aqueous solubility at physiological pH limits its concentration to about 40–60 mg/dL. It is important to avoid saturation with tyrosine to prevent formation of crystals. TPN compositions include sterilized powders for formulation into sterile TPN solutions.

The present invention also provides TPN solutions and compositions wherein cysteine is supplemented or replaced by γ-GluCys in an amount effective to provide a patient with a sufficient nutritional level of free cysteine. Additionally, the amount of γ-GluCys can provide a normal Cys/Met ratio, optionally, by also reducing the amount of methionine. Further the glutamic acid content of the TPN solutions can be reduced. In a preferred embodiment, γ-GluCys is γ-Glu(Cys)$_2$ or (γ-GluCys)$_2$ and provided in an amount needed for adequate nutrition, which is about 150 to about 600 mg/dL. In general, cysteine is not also present in TPN solutions because it oxidizes to form insoluble cysteine. TPN compositions include sterilized powders for formulation into sterile TPN solutions.

Another embodiment of the present invention provides TPN solutions and compositions wherein glutamine is provided by γ-GluGln in an amount effective to provide a patient with a sufficient nutritional level of free glutamine. Additionally, the amount of γ-GluGln can provide a normal Gln/Glu ratio, optionally by also reducing the amount of glutamic acid (glutamate) in the TPN solution. In a preferred embodiment, the amount of γ-GluGln needed for adequate nutrition is about 150 to about 1000 mg/dL, although higher levels may be required to normalize the plasma aminogram. In general glutamine is not present in the TPN solution, since its aqueous stability at physiological pH leads to formation of ammonia. TPN compositions include sterilized powders for formulation into sterile TPN solutions.

Further, in another preferred embodiment the present invention provides TPN solutions and compositions wherein tyrosine, cysteine and glutamine or any combination of these compounds, are simultaneously supplemented, replaced or included as provided above for each individual compound.

The pharmaceutical forms suitable for intravenous use include sterile aqueous solutions and sterile powders for the extemporaneous preparation of sterile solutions. In all cases the form must be sterile and the solution must be fluid to provide for easy flow. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils or other compounds compatible in intravenous administration. The solvent for amino acid mixtures is generally water with the pH adjusted to 5–6.5. The proper fluidity shall be maintained. Prevention of the action of microorganisms can be brought about by various antibacterial and antifungal agents, for example, parabens, chlorobutanol, phenol, sorbic acid, thimerosal, and the like. Preferably, however, the solution is sterilized by ultrafiltration. The osmotic pressure of the solution should be compatible with maintenance of healthy blood cells and tissues.

Sterile solutions are prepared by incorporating the active compounds in the required amount in the appropriate solvent with various of the other ingredients enumerated above, as required, followed by sterilization by ultrafiltration. In the case of sterile powders for the preparation of sterile solutions, the preferred methods of preparations are vacuum-drying and the freeze-drying technique which yield a powder of the active ingredient plus any additional desired ingredient from previously sterile-filtered solution thereof.

The examples further illustrate the invention.

EXAMPLE 1

γ-GluTyr Stability

A. In aqueous solution: A preliminary experiment was conducted to determine the elution characteristics of phenylalanine, tyrosine, and γ-GluTyr by the HPLC method for direct determination of plasma phenylalanine and tyrosine as described by Hilton, M. A. (1982) *Clin. Chem.* 28:1215–1218. The results of elution over a C-18 reverse phase column eluted with 18.1 % methanol in 0.085% phosphoric acid resulted in the elution profile shown in Table 3. As indicated by Hilton, supra, phenylalanine and tyrosine can be detected in as little as 30 μl of plasma by this method.

B. In a TPN amino acid solution: Equal volumes of 1.8 mM γ-GluTyr and Aminosyn-PF 10% (Abbott Laboratories) were mixed and the pH was adjusted to 5.5. The mixture thus contained similar concentrations of the peptide and of several amino acids, including phenylalanine and histidine. A sample was taken for analysis, and the remainder of the solution was sterilized by ultrafiltration and stored at room temperature (typical storage conditions for TPN amino acid solutions). Samples for analysis were also taken at intervals over a nine-month period. All samples were analyzed by HPLC as described above. The results indicated that the levels of γ-GluTyr and tyrosine were unchanged during the entire course of the experiment, and hence that the stability of γ-GluTyr is comparable to that of the amino acids in the solution, with no breakdown to release tyrosine, which might then have precipitated and been a hazard in the TPN solution.

TABLE 3

| Sample | HPLC Separations[a] | |
|---|---|---|
| | retention time (min) | pmoles per mm peak height (0.02 AUFS) |
| Tyr | 6.9 | 2.09 |
| Phe | 13.0 | 3.65 |
| γ-GluTyr | 11.5 | 2.15 |

[a] Elution conditions were 18.1% methanol in 0.085% phosphoric acid at a flow rate of 1 ml/min on a C-18 reverse phase column. Detection was at 206 nm.

EXAMPLE 2

Clearance of γ-GluTyr from Plasma

Injections of 20 μl of 140 mM γ-GluTyr (2.8 μmol) were made in the external jugular vein of 30–40 g mice. The amount of γ-GluTyr was measured in the plasma at 10 min and 60 min post-injection in each animal. The clearance of γ-GluTyr from plasma during this period was 2.2–2.6 μM/min.

Injection of twice as much γ-GluTyr (40 μl of 140 mM) in the same manner resulted in a clearance rate of 6.8 μM/min. In this experiment, the plasma concentration of tyrosine increased 32% between 5 and 10 min post-injection and then fell by 32% between 10 and 60 min. These results suggest that tyrosine is being released from γ-GluTyr and accumulating in the plasma during the time when the γ-GluTyr plasma level is highest; as plasma γ-GluTyr levels decrease, the liver is apparently metabolizing the excess tyrosine efficiently so that plasma tyrosine levels return to normal.

In another experiment, mice were injected with saline as a control or 2.8 μmol γ-GluTyr to compare plasma concentrations of tyrosine. The levels of tyrosine and phenylalanine were measured at 10 min post-injection (Table 4) and indicate that a significant increase in plasma tyrosine occurred in the mouse which received γ-GluTyr whereas at the same time the plasma level of phenylalanine was not significantly altered in the mice receiving γ-GluTyr as compared to saline-treated controls. Thus the marked increase in plasma tyrosine in animals injected with γ-GluTyr is consistent with release of tyrosine from the peptide and not to a generalized increase in plasma amino acids.

TABLE 4

Plasma Tyrosine Released from γ-GluTyr

| Experiment | Injection | Plasma[a] Tyr (μM) | Phe (μM) |
|---|---|---|---|
| A | 20 μL 0.15M NaCl | 65 ± 10 | 77 ± 5 |
| B | 20 μL 140 mM γ-GluTyr | 126 ± 14 | 89 ± 8 |

[a]10 min post-injection of γ-GluTyr.

EXAMPLE 3

Distribution of γ-GluTyr in Urine and Plasma

Urine was collected from mice injected with γ-GluTyr to determine whether or not the peptide was excreted into the urine. Mice were anesthetized with pentobarbital and then injected with 20 μl 140 mM γ-GluTyr (2.8 μmol). No urine was voided during the 60-min experiment, during which time the mice remained anesthetized. At the end of the experiment, the urinary bladders were tied off, removed and blood was collected from the heart for analysis. At the end of 60 min, a maximum of 0.13% of the injected γ-GluTyr was excreted in the urine whereas the plasma contained 12–25 μM γ-GluTyr. If these mice are assumed to have a total plasma volume of 4 ml, then only about 4% of the injected γ-GluTyr remained in the plasma at 60 min post-injection. Since a negligible amount of the total γ-GluTyr was lost in the urine, then at least 96% of the peptide had apparently been hydrolyzed and was available for use as free tyrosine and glutamic acid.

Previous studies had shown that the peptide is not partitioned into red blood cells, so the γ-GluTyr in the plasma represents the total amount present in the blood.

EXAMPLE 4

Role of γ-glutamyl transpeptidase in γ-GluTyr metabolism

The most likely route for metabolic degradation of γ-GluTyr involves the enzyme, γ-glutamyl transpeptidase (γ-GTase), a widely distributed enzyme in mammalian tissues. In an in vitro test of this hypothesis, γ-GluTyr was added to Aminosyn-PF 10% and the solution treated with bovine kidney γ-GTase (Sigma Type II) at pH 7.4. The results demonstrated that the enzyme released tyrosine from γ-GluTyr as monitored by HPLC.

To test the role of γ-GTase in degradation of γ-GluTyr in vivo an additional experiment was conducted. In this experiment mice were injected with a potent inhibitor of γ-GTase, acivicin, prior to administration of γ-GluTyr and the levels of the peptide, tyrosine and phenylalanine in plasma were monitored. Control mice received saline rather than acivicin prior to intravenous injection of 2.8 μmol of γ-GluTyr. In test mice, an intraperitoneal injection of acivicin was made 90 min prior to the injection of 2.8 μmol γ-GluTyr. Plasma was sampled after 10 min and 60 min, and urine was collected after 60 min. The results are shown in Table 5. The finding that the γ-GluTyr concentration was significantly higher and the tyrosine concentration significantly lower in the mice treated with acivicin compared to controls (compare experiments 1 and 2) supports the hypothesis that γ-GTase participates in the in vivo release of tyrosine from γ-GluTyr injected intravenously, and the inhibitor interferes with enzyme action.

The kidney is generally unable to prevent the loss of intact peptides in the urine. Instead, peptides are hydrolyzed to free amino acids, which can then be salvaged by absorption into the bloodstream. In the case of γ-GluTyr, γ-GTase, which is very active in the kidney, can hydrolyze the peptide to release free glutamic acid and tyrosine, which the kidney can then return to the blood. When γ-GTase is inhibited by acivicin, unhydrolyzed peptide should be lost in the urine. The data in Table 5 are consistent with a role for γ-GTase in the hydrolysis of γ-GluTyr to prevent its excretion in the urine. When this enzyme is inhibited by acivicin, the amount of unhydrolyzed peptide which appears in the urine in 60 min increases markedly over peptide found in the urine of control mice.

TABLE 5

Effects of Inhibiting γ-GTase in mice injected with γ-GluTyr[a]

| Experiment | Acivicin[b] | Tyr (μM) | γ-GluTyr (μM) | Phe (μM) | γ-GluTyr[c] excreted (% of total) |
|---|---|---|---|---|---|
| 1 | + | 96 ± 1 | 247 ± 17 | 96 ± 6 | 16–48 |
| 2 | − | 126 ± 14 | 112 ± 15 | 89 ± 8 | 0.05–0.19 |

[a]Plasma concentrations at 10 min post-injection of γ-GluTyr.
[b]Acivicin (2 mg/30 g mouse) was injected i.p. 90 min before the peptide was injected i.v.
[c]Percent γ-GluTyr lost in the urine at 60 min post-injection.

EXAMPLE 5

γ-GluCys Stability

Measurement of total glutathione, cysteine, and γ-Glu-(Cys)$_2$ or (γ-Glu-Cys)$_2$ in plasma is accomplished by modification of HPLC methods coupled with sensitive fluorescence detection [Svardal et al. (1990), *Anal.*

Biochem. 184: 338-346]. These molecules are measured after they are freed from -S-S- linkages to each other or to proteins.

A preliminary experiment is conducted to determine the stability of γ-Glu(Cys)$_2$ in sterile aqueous solution at pH 5.5 to 6.0. At intervals of time over several months, an aliquot of the sample which has been stored at room temperature (typical storage conditions for TPN amino acid solutions) is taken for analysis by HPLC as indicated above. Because Amino Syn-PF 10% contains sodium hydrosulfite which reacts with thiols or disulfides, the stability of γ-Glu (Cys) cannot be tested in Aminosyn-PF 10%.

EXAMPLE 6

Clearance of γ-GluCys from Plasma,

The clearance of γ-Glu(Cys)$_2$ or ( γ-GluCys)$_2$ from plasma is conducted as described in Example 2 for γ-GluTyr except that the cysteine compounds are substituted for γ-GluTyr.

EXAMPLE 7

In Vivo Release of free Tyrosine from γ-GluTyr During TPN

A rat was implanted with a catheter into the inferior vena cava via the femoral vein on day 0. After recovery from surgery the rat was allowed free access to rat chow and water while physiological saline was delivered via the catheter. All solutions were delivered at 2-3 ml/h. On day 3, a blood sample was drawn and the catheter infusion was switched to a standard TPN formulation (standard TPN). Blood samples were withdrawn at 48 and 96 h after TPN administration for analysis of plasma amino acids. After 96 h of standard TPN, the amino acid mixture of the formulation was changed to a mixture containing γ-GluTyr, (GluTyr TPN, 13 mM) at 4 g/h of TPN or 535 mg/dl of amino acid solution. Every 24 h a blood sample was withdrawn for analysis of plasma amino acids. After 72 h of GluTyr TPN at the 13 mM concentration, the GluTyr TPN was reduced by half (i.e., to 6.5mM γ-GluTyr) and continued an additional 24 h. A blood sample was withdrawn, then 8 min later the infusion was stopped and another blood sample withdrawn (i.e., the end sample).

The standard TPN formulation contained:

| | |
|---|---|
| Glucose | 17.5% |
| Amino Acids (Aminosyn-PF 10%) | 3.8% |
| Lipid (Liposyn II-20%) | 2.9% |

Vitamins, electrolytes, trace elements and choline were also included. The standard TPN solution was delivered at a rate of 252 cal/kg body wt/day and thus provided:

| | |
|---|---|
| Lipid | 320.1 cal/1 |
| Carbohydrate | 583.1 cal/1 |
| Amino acids | 151.2 cal/1 |
| Total | 1054.4 cal/1 |
| Non-protein calories per g N: | 150 |
| Nitrogen: | 1.46 g/kg body wt/day |
| Calories from lipid: | 30.4% |

The GluTyr TPN formulation was identical to the standard TPN formulation except that a special formulation of Aminosyn-PF 10% was used which contained γ-GluTyr with reduced amounts of phenylalanine and glutamic acid. The exact compositions are indicated in Table 6.

The results of this experiment are provided in Table 7 and indicate that the levels of free tyrosine in plasma increased significantly upon administration of the Glu(-Tyr) TPN solution containing γ-GluTyr relative to the standard TPN solution. Concomitantly the levels of free phenylalanine and tryptophan remained near the levels obtained from chow feeding. At the lower γ-GluTyr dose the plasma Phe/Tyr ratio was normalized. Overall the rat tolerated the GluTyr TPN with no detectable problems for over 72 h and continued to gain weight during that period.

TABLE 6

Composition of Aminosyn-PF 10% for Standard TPN and Glu(Tyr) TPN[a]

| Amino Acids[b] | Standard TPN | | GluTyr TPN (13 mM) | | GluTyr TPN (6.5 mM) | |
|---|---|---|---|---|---|---|
| | mg/100 mL | mM | mg/100 ml[c] | mM | mg/100 ml | mM |
| *Essential:* | | | | | | |
| Arg | 1227 | 70.4 | — | — | — | — |
| His | 312 | 20.1 | — | — | — | — |
| Ise | 760 | 57.9 | — | — | — | — |
| Leu | 1200 | 91.5 | — | — | — | — |
| Lys | 677 | 46.3 | — | — | — | — |
| Met | 180 | 45.4 | — | — | — | — |
| Phe | 427 | 25.8 | 217 | 13.1 | 217 | 13.1 |
| Thr | 512 | 43.0 | — | — | — | — |
| Try | 180 | 8.8 | — | — | — | — |
| Val | 673 | 57.4 | — | — | — | — |
| Total essential: | | 466.6 | | 453.9 | | 453.9 |
| *Nonessential:* | | | | | | |
| Ala | 898 | 100.8 | — | — | — | — |
| Asp | 527 | 39.6 | — | — | — | — |
| Glu | 820 | 55.7 | 625 | 42.5 | 625 | 42.5 |
| Gly | 385 | 51.3 | — | — | — | — |
| Pro | 812 | 61.9 | — | — | — | — |
| Ser | 495 | 47.1 | — | — | — | — |
| Tau | 70 | 5.6 | — | — | — | — |
| Tyr | 44 | 2.4 | 44 | 2.4 | 44 | 2.4 |
| γ-GluTyr | | | 1070 | 34.5 | 535 | 17.2 |
| Total nonessential: | | 364.4 | | 368.2 | | 359.7 |

TABLE 6-continued

| | Composition of Aminosyn-PF 10% for Standard TPN and Glu(Tyr) TPN[a] | | | | | |
|---|---|---|---|---|---|---|
| | Standard TPN | | GluTyr TPN (13 mM) | | GluTyr TPN (6.5 mM) | |
| Amino Acids[b] | mg/100 mL | mM | mg/100 ml[c] | mM | mg/100 ml | mM |
| | TOTAL: | 831.0 | | 822.1 | | 813.6 |

[a]The standard TPN formulation is that of Aminosyn-PF 10%. The Glu(Tyr) TPN formulation is identical to the Aminosyn-PF 10% except as indicated.
[b]Lysine was added as the acetate salt. Tau, Taurine.
[c]A "—" indicates that the amount of amino acid is unchanged relative to the standard TPN formulation.

TABLE 7

| | Amino Acids Released During TPN | | | | |
|---|---|---|---|---|---|
| Blood Sample | Tyr[a] | γ-GluTyr | Phe | Trp | Phe/Tyr |
| Pre-TPN (chow fed) | 107 | — | 83 | 83 | 0.77 |
| Standard TPN, 48 h | 55 | — | 97 | 61 | 1.76 |
| Standard TPN, 96 h | 39 | — | 104 | 59 | 2.68 |
| Glu(Tyr) TPN (13 mM) | | | | | |
| 24 h | 170 | 54 | 82 | 75 | 0.40 |
| 48 h | 165 | 100 | 65 | 91 | 0.39 |
| 72 h | 165 | 89 | 62 | 87 | 0.38 |
| Glu(Tyr) TPN (6.5 mM) | | | | | |
| 24 h | 87 | 28 | 67 | 64 | 0.77 |
| End | 90 | 21 | 69 | 72 | 0.77 |

[a]All concentrations are in μM.

EXAMPLE 8

γ-GluGln Stability

Measurement of γ-GluGln, glutamine and glutamic acid in plasma is accomplished by modification of HPLC methods for amino acid analysis coupled with sensitive fluorescence detection [Larsen et al. (1980) J. Chromatogr. Sci. 18:233–236] or accomplished by standard amino acid analysis techniques.

To determine the stability of γ-GluGln under typical storage conditions, γ-GluGln was added to Aminosyn-PF 10% under sterile conditions and left at room temperature. At one month, 4.5 and 9 months later, γ-GluGln remained stable in the solution, i.e. no significant break down or decomposition had occurred.

EXAMPLE 9

Clearance of γ-GluGln from Plasma

Mice were injected with 29 μmoles of γ-GluGln via the external jugular vein. Control animals were injected with an equal volume of saline. Blood was sampled at 10 min. and at 60 min after injection. Plasma amino acids were determined by amino acid analysis. γ-GluGln was detected in the plasma of only three of six mice at 10 min, suggesting that the peptide was efficiently degraded. Additionally, γ-GluGln did not appear in the urine unless the mice were pretreated with acivicin, an inhibitor of γ-GTase.

The plasma glutamine levels were measured and the results are provided in Table 8. The plasma concentration of glutamine in animals injected with γ-GluGln was significantly higher at 10 min relative to 60 min post injection. Similarly, the mice which received γ-GluGln exhibited significantly higher glutamine levels at 10 min post injection relative to the control group (saline injected) at 10 min post injection.

TABLE 8

| | Release of Plasma Glutamine | |
|---|---|---|
| | Glutamine Concentration (μM) | |
| Experiment | 10 min | 60 min |
| Control Mice (N = 6) (saline) | 572 | 583 |
| | 418 | 485 |
| | 522 | 540 |
| | 629 | 706 |
| | 461 | 480 |
| | 471 | 550 |
| Mean + Standard Error | 512 ± 32 | 557 ± 34 |
| Experimental Mice (N = 6) (γ-GluGln) | 675 | 565 |
| | 762 | 586 |
| | 614 | 457 |
| | 693 | 198 |
| | 681 | 555 |
| | 770 | 629 |
| Mean + Standard Error | 699 ± 24 | 498 ± 64 |

I claim:

1. A method for total parenteral nutrition (TPN) of a patient which comprises administering to said patient γ-glutamyltyrosine in a TPN solution in an amount effective to provide a sufficient nutritional level of free tyrosine in said patient.

2. The method of claim 1, which further comprises administering tyrosine in said TPN solution, wherein said tyrosine and said γ-glutamyltyrosine provide a sufficient nutritional level of free tyrosine in said patient.

3. The method of claim 1, wherein said γ-glutamyltyrosine is γ-L-glutamyl-L-tyrosine.

4. The method of claim 1, wherein said patient is a human.

5. The method of claim 1, wherein said patient is an animal.

6. The method of claim 1, wherein said sufficient nutritional level of free tyrosine provides a plasma level of free tyrosine equivalent to the level of free tyrosine provided by dietary protein.

7. The method of claim 1, wherein said γ-glutamyltyrosine is present in said TPN solution at about 150 mg/dl to about 600 mg/dl.

8. The method of claim 1, wherein said γ-glutamyltyrosine is present in said solution at about 150 mg/dl to about 600 mg/dl.

9. The method of claim 1, wherein the amount of phenylalanine or glutamic acid in said TPN solution is adjusted by an amount effective to compensate for the presence of γ-glutamyltyrosine.

10. The method of claim 2, wherein said tyrosine and said γ-glutamyltyrosine are present in said TPN solution at a sum total of about 150 mg/dl to about 600 mg/dl.

11. The method of claim 2, wherein said tyrosine and said γ-glutamyltyrosine are present in said solution at a sum total of about 150 mg/dl to about 750 mg/dl.

12. A method for total parenteral nutrition (TPN) of a patient which comprises administering to said patient γ-glutamylcysteine in a TPN solution in an amount effective to provide a sufficient nutritional level of cysteine in said patient.

13. The method of claim 12, which further comprises administering cysteine or cysteine in said TPN solution, wherein said cysteine, said cysteine, and said γ-glutamylcysteine provide a sufficient nutritional level of cysteine in said patient.

14. The method of claim 12, wherein said γ-glutamylcysteine is γ-L-glutamyl-L-cysteine or N,N'-bis(γ-L-glutamyl)-L-cysteine.

15. The method of claim 12, wherein said patient is a human.

16. The method of claim 12, wherein said patient is an animal.

17. The method of claim 12, wherein said sufficient nutritional level of cysteine provides a plasma level of cyst(e)ine equivalent to the level of cyst(e)ine provided by dietary protein.

18. The method of claim 12, wherein said γ-glutamylcysteine is present in said TPN solution at about 150 mg/dl to about 600 mg/dl.

19. The method of claim 12, wherein the amount of methionine or glutamic acid in said TPN solution is adjusted by an amount effective to compensate for the presence of γ-glutamylcysteine.

20. The method of claim 13, wherein said cysteine, said cystine, and said γ-glutamylcysteine are present in said TPN solution at a sum total of about 150 to about 600 mg/dl.

21. A method for total parenteral nutrition (TPN) of a patient which comprises administering to said patient a TPN solution comprising at least one of the peptides γ-glutamyltyrosine or γ-glutamylcysteine effective in an amount to provide sufficient nutrition in said patient.

22. The method of claim 21, wherein said γ-glutamyltyrosine is γ-L-glutamyl-L-tyrosine.

23. The method of claim 21, wherein said γ-glutamylcysteine is γ-L-glutamyl-L-cysteine or N,N'-bis(γ-L-glutamyl)cysteine.

24. The method of claim 21, wherein said patient is a human.

25. The method of claim 21, wherein said patient is an animal.

26. The method of claim 21, wherein said γ-glutamyltyrosine or said γ-glutamylcysteine are each present in said TPN solution at about 150 mg/dl to about 600 mg/dl.

27. The method of claim 21, wherein said γ-glutamyltyrosine is present in said solution at about 150 mg/dl to about 750 mg/dl.

28. The method of claim 21, wherein said γ-glutamylcysteine is present in said solution at about 150 mg/dl to about 600 mg/dl.

29. A composition for total parenteral nutrition comprising an effective amount of each of at least one of the peptides γ-glutamyltyrosine to provide a sufficient nutritional level of tyrosine or γ-glutamylcysteine to provide a sufficient nutritional level of cysteine or a combination of both.

30. The composition of claim 29, wherein said composition is an aqueous solution.

31. The composition of claim 29, wherein said γ-glutamyltyrosine is γ-L-glutamyl-L-tyrosine.

32. The composition of claim 29, wherein said γ-glutamylcysteine is γ-L-glutamyl-L-cysteine or N,N'-bis(γ-L-glutamyl)cysteine.

33. The composition of claim 30, wherein said γ-glutamyltyrosine or γ-glutamylcysteine are each present in a concentration of about 150 mg/dl to about 600 mg/dl.

34. The composition of claim 30, wherein said γ-glutamyltyrosine is present in a concentration of about 150 mg/dl to about 750 mg/dl, or wherein said γ-glutamylcysteine is present in a concentration of about 150 mg/dl to about 600 mg/dl.

35. The composition of claim 33, wherein γ-glutamyltyrosine and γ-glutamylcysteine are present in said composition.

36. The composition of claim 29, wherein said composition is a sterile powder.

37. The composition of claim 36, wherein said γ-glutamyltyrosine or γ-glutamylcysteine or a combination of each is present in an amount to provide said γ-glutamyltyrosine or said γ-glutamylcysteine at a concentration of each at about 150 mg/dl to about 600 mg/dl when said powder is formulated into a solution.

38. The composition of claim 36, wherein said γ-glutamyltyrosine or γ-glutamylcysteine or a combination of each is present in an amount to provide said γ-glutamyltyrosine at a concentration of about 150 mg/dl to about 750 mg/dl, or to provide said γ-glutamylcysteine at a concentration of about 150 mg/dl to about 600 mg/dl when said powder is formulated into a solution.

39. A composition for total parenteral nutrition comprising an effective amount of γ-glutamyltyrosine to provide a sufficient nutritional level of tyrosine.

40. The composition of claim 39 wherein said γ-glutamyltyrosine is present at a concentration of about 150 mg/dl to about 750 mg/dl.

41. A composition for total parenteral nutrition comprising an effective amount of γ-glutamylcysteine to provide a sufficient nutritional level of cysteine.

42. The composition of claim 41 wherein said γ-glutamylcysteine is present at a concentration of about 150 mg/dl to about 600 mg/dl.

* * * * *

UNITED STATES PATENT AND TRADEMARK OFFICE
CERTIFICATE OF CORRECTION

PATENT NO. : 5,206,220
DATED      : April 27, 1993
INVENTOR(S) : Mary A. Hilton

It is certified that error appears in the above-indentified patent and that said Letters Patent is hereby corrected as shown below:

On the Title page, item [63] insert -- [30] Foreign/PCT APPLICATION PRIORITY DATE
April 23, 1991                    PCT/US 91/02777

Column 4, line 19, "$\gamma$-glutamyl" should read --$\partial$-glutamyl--
Column 6, line 57, after "of" insert --cysteine in--
Column 15, line 35, "cysteine" should --cystine--.
Column 16, line 41, "1.8" should read --21.8--.
Column 23, lines 7 and 8, Claim 13, "cysteine" should read --cystine--.

Signed and Sealed this

First Day of February, 1994

Attest:

BRUCE LEHMAN

Attesting Officer

Commissioner of Patents and Trademarks